United States Patent
Feinstein et al.

(10) Patent No.: US 12,063,914 B2
(45) Date of Patent: *Aug. 20, 2024

(54) DNA SEQUENCE THAT INCREASES ODORANT RECEPTOR REPRESENTATION IN THE OLFACTORY SYSTEM

(71) Applicant: Research Foundation of the City University of New York, New York, NY (US)

(72) Inventors: Paul Feinstein, New York, NY (US); Charlotte D'Hulst, Brooklyn, NY (US)

(73) Assignee: Paul Feinstein, New York, NY (US)

( * ) Notice: Subject to any disclaimer, the term of this patent is extended or adjusted under 35 U.S.C. 154(b) by 768 days.

This patent is subject to a terminal disclaimer.

(21) Appl. No.: 16/704,740

(22) Filed: Dec. 5, 2019

(65) Prior Publication Data

US 2020/0093104 A1 Mar. 26, 2020

Related U.S. Application Data

(63) Continuation of application No. 15/749,007, filed as application No. PCT/US2016/045338 on Aug. 3, 2016, now Pat. No. 10,512,253.

(60) Provisional application No. 62/312,068, filed on Mar. 23, 2016, provisional application No. 62/200,312, filed on Aug. 3, 2015.

(51) Int. Cl.
*C12N 15/85* (2006.01)
*A01K 67/0275* (2024.01)

(52) U.S. Cl.
CPC .......... *A01K 67/0275* (2013.01); *C12N 15/85* (2013.01); *C12N 15/8509* (2013.01); *A01K 2217/072* (2013.01); *A01K 2217/20* (2013.01); *A01K 2227/10* (2013.01); *A01K 2267/02* (2013.01)

(58) Field of Classification Search
None
See application file for complete search history.

(56) References Cited

U.S. PATENT DOCUMENTS

2010/0222561 A1 9/2010 Matsunami et al.

FOREIGN PATENT DOCUMENTS

| JP | 2018-530997 | 10/2018 |
|---|---|---|
| WO | WO 0017371 | 3/2000 |
| WO | WO0151609 | 7/2001 |
| WO | WO2006002161 | 1/2006 |
| WO | WO 2014210585 | 12/2014 |
| WO | WO 2017024028 | 2/2017 |

OTHER PUBLICATIONS

Vassalli et al Molecular and Cellular Neuroscience 46 (2011) 381-396 (Year: 2011).*
Potaman et al DNA: Alternative confirmations and Biology, Madame Curie Bioscience Database, 1-17 (Year: 2013).*
DHulst et al Cell Report 16, 115-1125 (Year: 2016).*
Rothman et al Mol. Cell Neurosci 525-546 (Year: 2005).*
D'Hulst, C. Et Al.; MouSensor: A Versatile Genetic Platform to Create Super Sniffer Mice for Studying Human Odor Coding; Cell Reports; Jul. 26, 2016; pp. 1115-1125; vol. 16.
Bozza, T. Et Al.; Mapping of Class I and Class II Odorant Receptors to Glomerular Domains by Two Distinct Types of Olfactory Sensory Neurons in the Mouse; Neuron; Jan. 29, 2009; pp. 1-24; 61(2).
Fleischmann, A. Et Al.; Mice with a "Monoclonal" Nose: Perturbations in an Olfactory Map Impair Odor Discrimination; Neuron; Dec. 26, 2008; pp. 1-25; 60(6).
Vassalli, A. Et Al.; Minigenes Impart Odorant Receptor-Specific Axon Guidance in the Olfactory Bulb; Neuron; Aug. 15, 2002; pp. 681-696, vol. 35; Cell Press.
Vassalli, A. Et Al.; Homeodomain binding motifs modulate the probability of odorant receptor gene choice in transgenic mice; Mol Cell Neurosci .; Feb. 2011; pp. 1-30; 46(2).
Degl'Innocenti, A. Et Al.; The Mouse Solitary Odorant Receptor Gene Promoters as Models for the Study of Odorant Receptor Gene Choice; PLOS One; Jan. 21, 2016; pp. 1-17; http://dx.doi.org/10.1371/journal.pone.0144698.
Rothman, A. Et Al.; The promoter of the mouse odorant receptor gene M71; Mol. Cell. Neurosci.; Jan. 8, 2005; pp. 535-546; vol. 28; Elsevier.
Saito, H. Et Al.; RTP Family Members Induce Functional Expression of Mammalian Odorant Receptors; Cell Nov. 24, 2004; pp. 679-691; vol. 119; Cell Press.
Nguyen, M. Et Al.; A Smell That Causes Seizure; PLoS One; Jul. 27, 2012; pp. 1-10; vol. 7; Issue 7; PLoS One.
Movahedi, K. Et Al.; Odorant receptors can mediate axonal identity and gene choice via cAMPindependent mechanisms; Open Biology; Jul. 2016; pp. 1-19; 6(7).
Fleischmann, A. Et Al.; Functional Interrogation of an Odorant Receptor Locus Reveals Multiple Axes of Transcriptional Regulation; PLOS; May 21, 2013; pp. 1-14; vol. 11, Issue 5.
Von Der Weid, B. Et Al.; Large-scale transcriptional profiling of chemosensory neurons identifies receptor-ligand pairs in vivo; Nature Neuroscience; Aug. 31, 2015; pp. 1-14; vol. 18.
Genbank; Mus musculus H-region enhancer sequence for "Negative feedback regulation ensures the one receptor-one olfactory neuron rule in mouse"; Jun. 28, 2005; Version: DQ086467.1 GI 68160280; 1 Page.

(Continued)

*Primary Examiner* — Anoop K Singh
(74) *Attorney, Agent, or Firm* — Peter J. Mikesell; Schmeiser, Olsen & Watts, LLP (57) ABSTRACT

A genetically modified vertebrate is provided that has an enhanced sense due to an over representation of a predetermined odorant receptor. The vertebrate is genetically modified by introduction of DNA that comprises at least four sequential repeats of a sequence whose primary structure is at least 90% homologous with ACATAACTTTTTAATGAGTCT (SEQ ID NO: 1). The DNA causes a nearby odorant receptor coding sequence to be over represented in a singular gene choice fashion relative to a corresponding vertebrate that lacks the DNA.

6 Claims, 4 Drawing Sheets
Specification includes a Sequence Listing.

(56) References Cited

OTHER PUBLICATIONS

Serizawa, S. Et Al.; Negative Feedback Regulation Ensures the One Receptor-One Olfactory Neuron Rule in Mouse; Science; Dec. 19, 2003; pp. 2088-2094; vol. 302.

ISA/US; International Search Report/Written Opinion mailed Oct. 31, 2016 in International Application PCT/US16/45338; 8 pages.

Khan, M. Et Al.; Regulation of the Probability of Mouse Odorant Receptor Gene Choice; Cell; Sep. 19, 2011; pp. 907-921; vol. 147, No. 4.

Serizawa, S. Et Al.; One Neuron-one receptor rule in the mouse olfactory system; Trends In Genetics; Oct. 6, 2004; pp. 648-653; vol. 20, No. 12.

Feinstein, P. Et Al.; A Contextual Model for Axonal Sorting into Glomeruli in the Mouse Olfactory System; Cell; Jun. 11, 2004; pp. 817-831; vol. 117.

Sato, Y. Et Al.; Hierarchical Regulation of Odorant Receptor Gene Choice and Subsequent Axonal Projection of Olfactory Sensory Neurons in Zebrafish; the Journal of Neuroscience; Feb. 14, 2007; pp. 1606-1615; vol. 27, No. 7.

EPO; Extended European Search Report for corresponding EP Application 16833802.8 issued Mar. 25, 2019.

Mina, R. Et Al.; Investigating the Mechanisms of Singularity of Odorant Receptor Gene Choice; Chemical Senses; Feb. 3, 2018; pp E16-E17; vol. 43, No. 3.

Iwata, T. Et Al.; A long-range cis-regulatory element for class I odorant receptor genes; Nature Communications; Oct. 12, 2017; pp. 1-12; vol. 8, No. 1.

Gun, G. Et Al.; Current Progress of Genetically Engineered Pig Models for Biomedical Research; BioResearch Open Access; Dec. 2014; pp. 255-264; vol. 3, No. 6.

Park, K. Et Al.; Role of stem cells in large animal genetic engineering in the TALENs-CRISPR era; Reproduction, Fertility and Development; 2014; pp. 65-73.

Prather, R. Et Al.; Genetically Engineered Pig Models for Human Diseases; Annu Rev Anim Biosci.; Jan. 2013; pp. 203-219.

Graham, D. Et Al.; Resources for the design of CRISPR gene editing experiments; Genome Biology; 2015; pp. 1-21; 16:260.

Sieren, J. Et Al.; Development and translational imaging of a TP53 porcine tumorigenesis model,; JCI; 2014; pp. 4052-4066; vol. 124, No. 9.

Whitelaw, C. Et Al.; Engineering large animal models of human disease; J. Pathol; Nov. 28, 2015; pp. 247-256; vol. 238.

Leuchs, S. Et Al.; Inactivation and Inducible Oncogenic Mutation of p53 in Gene Targeted Pigs; PLOS; Oct. 5, 2012; 8 pages; vol. 7, Issue 10.

* cited by examiner

*All mice are homozygous for the gene-targeted M71-IREStauGFP (M71G -/-)

```
                          SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA fragment for enhancing expression
      of a nearby odorant receptor coding sequence.

<400> SEQUENCE: 1
acataacttt ttaatgagtc t                                           21

<210> SEQ ID NO 2
<211> LENGTH: 13
<212> TYPE: DNA
<213> ORGANISM: Artificial Sequence
<220> FEATURE:
<223> OTHER INFORMATION: 13mer binding site within the homeodomain (HD)

<400> SEQUENCE: 2
aactttttaa tga                                                    13

<210> SEQ ID NO 3
<211> LENGTH: 18
<212> TYPE: DNA
<213> ORGANISM: Artificial Sequence
<220> FEATURE:
<223> OTHER INFORMATION: Forward primer for use in PCR.

<400> SEQUENCE: 3
ccctggacaa catcacac                                               18

<210> SEQ ID NO 4
<211> LENGTH: 25
<212> TYPE: DNA
<213> ORGANISM: Artificial Sequence
<220> FEATURE:
<223> OTHER INFORMATION: Reverse primer for use in PCR.

<400> SEQUENCE: 4
ccctccatgt gcaccttgaa gcgca                                       25

<210> SEQ ID NO 5
<211> LENGTH: 22
<212> TYPE: DNA
<213> ORGANISM: Artificial Sequence
<220> FEATURE:
<223> OTHER INFORMATION: Reverse primer used in PCR.

<400> SEQUENCE: 5
cgtttacgtc gccgtccagc tc                                          22

<210> SEQ ID NO 6
<211> LENGTH: 25
<212> TYPE: DNA
<213> ORGANISM: Artificial Sequence
<220> FEATURE:
<223> OTHER INFORMATION: Forward primer for use in PCR.
```

```
<400> SEQUENCE: 6
ccgcactgga caaaacactg aggag                                          25

<210> SEQ ID NO 7
<211> LENGTH: 24
<212> TYPE: DNA
<213> ORGANISM: Artificial Sequence
<220> FEATURE:
<223> OTHER INFORMATION: Reverse primer for use in PCR.

<400> SEQUENCE: 7
ctgtttcctg ttcagagttg ggtg                                           24

<210> SEQ ID NO 8
<211> LENGTH: 21
<212> TYPE: DNA
<213> ORGANISM: Artificial Sequence
<220> FEATURE:
<223> OTHER INFORMATION: Forward primer for use in PCR.

<400> SEQUENCE: 8
tgtgaggcaa ttgacatgtg g                                              21

<210> SEQ ID NO 9
<211> LENGTH: 19
<212> TYPE: DNA
<213> ORGANISM: Artificial Sequence
<220> FEATURE:
<223> OTHER INFORMATION: Reverse primer for use in PCR.

<400> SEQUENCE: 9
tacggtgagt ctgtgtcac                                                 19

<210> SEQ ID NO 10
<211> LENGTH: 19
<212> TYPE: DNA
<213> ORGANISM: Artificial Sequence
<220> FEATURE:
<223> OTHER INFORMATION: Synthetic DNA fragment that inconsistently
      increases cell numbers associated with the MOR23 transgene

<400> SEQUENCE: 10 acaactttt aatgaagtc                                                  19

<210> SEQ ID NO 11
<211> LENGTH: 110
<212> TYPE: DNA
<213> ORGANISM: Artificial Sequence
<220> FEATURE:
<223> OTHER INFORMATION: Artificial sequence comprising a five repeat
      for use as a forward ultramer.

<400> SEQUENCE: 11
ctagcacata actttttaat gagtctacat aactttttaa tgagtctaca taactttta     60 atgagtctac ataactttt aatgagtcta cataactttt taatgagtct                110

<210> SEQ ID NO 12
<211> LENGTH: 110
<212> TYPE: DNA
<213> ORGANISM: Artificial Sequence
<220> FEATURE:
<223> OTHER INFORMATION: Artificial sequence comprising a five repeat
      for use as a reverse ultramer.

<400> SEQUENCE: 12
```

```
ctagagactc attaaaaagt tatgtagact cattaaaaag ttatgtagac tcattaaaaa        60
gttatgtaga ctcattaaaa agttatgtag actcattaaa aagttatgtg                  110

<210> SEQ ID NO 13
<211> LENGTH: 491
<212> TYPE: DNA
<213> ORGANISM: Artificial Sequence
<220> FEATURE:
<223> OTHER INFORMATION: M71 promoter sequence

<400> SEQUENCE: 13
gctagctcat gatgcatcat ggtgactagc taacaatatg taataaccat catggcactg        60
agaatgatgt tgctggtagt tactgtggtg cctattgaga tgaaaatgac aataatgata       120
atacatcagt agtaaaggtg atagccatgg tcataatggt aatgatgata aggatgggtg       180
ggtagtggtg atggatggtt ggtggtggtg gtggtgatgg tagtggtagg ggggtaatgg       240
tggtggtaac ggctctgttg atgctaaatt gttcattgcc ccattatatt ctaagtttct       300
gaaactgaaa gatgactttt acagataaaa gaagaattaa cacacttggg aaataaaaca       360
tgattcacag aacaagagaa aacatgaact aattgttact ttagagacaa caatggtctc       420
tagagtgact atatcccagg agatgatcca cacacacaca cacatatata taaacagaac       480 ccccaattt t                                                             491

<210> SEQ ID NO 14
<211> LENGTH: 601
<212> TYPE: DNA
<213> ORGANISM: Artificial Sequence
<220> FEATURE:
<223> OTHER INFORMATION: 5x21 M71 Transgene Promotor

<400> SEQUENCE: 14
gctagcacat aacttttaa tgagtctaca taacttttta atgagtctac ataactttt         60 aatgagtcta cataactttt taatgagtct acataacttt ttaatgagtc tctagctcat      120
gatgcatcat ggtgactagc taacaatatg taataaccat catggcactg agaatgatgt      180
tgctggtagt tactgtggtg cctattgaga tgaaaatgac aataatgata atacatcagt      240
agtaaaggtg atagccatgg tcataatggt aatgatgata aggatgggtg ggtagtggtg      300
atggatggtt ggtggtggtg gtggtgatgg tagtggtagg ggggtaatgg tggtggtaac      360
ggctctgttg atgctaaatt gttcattgcc ccattatatt ctaagtttct gaaactgaaa      420
gatgactttt acagataaaa gaagaattaa cacacttggg aaataaaaca tgattcacag      480
aacaagagaa aacatgaact aattgttact ttagagacaa caatggtctc tagagtgact      540
atatcccagg agatgatcca cacacacaca cacatatata taaacagaac ccccaattt      600 t                                                                       601
```

DNA SEQUENCE THAT INCREASES ODORANT RECEPTOR REPRESENTATION IN THE OLFACTORY SYSTEM

CROSS-REFERENCE TO RELATED APPLICATIONS

This application claims priority to and is a continuation of U.S. patent application Ser. No. 15/749,007 (filed Jan. 30, 2018) which is U.S. national stage filing under 35 U.S.C. 371 of PCT/US16/45338 (filed Aug. 3, 2016) which claims priority to U.S. Patent Application 62/200,312 (filed Aug. 3, 2015) and 62/312,068 (filed Mar. 23, 2016) the entirety of which are incorporated herein by reference.

STATEMENT OF FEDERALLY SPONSORED RESEARCH OR DEVELOPMENT

This invention was made with government support under grant number GM088114-01A1 awarded by the National Institute of Health and grant number MD007599 awarded by the National Institute on Minority Health and Health Disparities. The government has certain rights in the invention.

REFERENCE TO A SEQUENCE LISTING

This application contains a Sequence Listing in computer readable form. The computer readable form is incorporated herein by reference.

BACKGROUND OF THE INVENTION

The subject matter disclosed herein relates to generating genetically modified organisms and, in particular, to genetically modified organisms with an increased representation of odorant receptors, which concomitantly enhances the sense of smell. Currently, animals such as dogs, bees and rats are deployed to help humans with scent detection tasks, but their use is expensive since they require long-term training. Having a genetically manipulated organism with an increased representation of specific odorant receptors will considerably shorten the training process and advance animal-based scent detection tasks. Having a genetically manipulated organism with an increased representation of specific odorant receptors increases researcher's ability to analyze odors that activate that particular odorant receptors.

Volatile chemicals are detected by several million olfactory sensory neurons (OSNs) arrayed in a sensory epithelium located inside the nasal cavity. The main olfactory epithelium (MOE) expresses odorant receptors (ORs) through a poorly understood singular gene choice mechanism whereby only one allele of any OR gene is selected for specific expression in a given neuron. Typically, ~0.1% of the total number of OSNs in the MOE expresses the same OR and their axons coalesce into homotypic glomeruli in the olfactory bulb, the first relay station for synaptic activity in the brain. Thus, all ORs being expressed in equal and low representation makes the olfactory neuronal sheet a broad, non-specific detector of odorants.

Several million olfactory sensory neurons (OSNs) in the nose are used to identify volatile chemicals (odors). Rodents and dogs carry about 1000 individual odorant receptor (OR) genes, whose proteins can bind to specific odors; roughly 10,000 neurons are associated with an individual OR gene. Thus, each OR is present in an equal and low representation (0.1%), which makes the olfactory neuronal sheet a broad, non-specific detector of odorants.

There has been limited success in odor profiling ORs expressed in heterologous cells in vitro. Part of this limitation is due to the inability of OR proteins to traffic to the plasma membrane. In addition, given the biological properties of the olfactory system many in vitro characterized OR alleles may not be functional in an in vivo setting. The major drawback, though, has been the ability to rapidly contrast how odors presented in liquid phase (in vitro) correspond to odors presented to the OR in vapor phase within their mucosal environment (in vivo). Even ex vivo patching of dendritic knobs from transgenic and gene-targeted mice suffers from an absence of vapor phase delivery of odors. In addition, the study of both OR gene choice and OR coding in vivo is hampered by the low representation of a given OR, i.e. only ~0.1% on average of the total neuronal population in a wild type mouse. A rapid in vivo approach to odor profile any OR would be a breakthrough and permit researchers to correlate in vitro, ex vivo, and in vivo responses. Unfortunately, no suitable in vivo approach is known.

The discussion above is merely provided for general background information and is not intended to be used as an aid in determining the scope of the claimed subject matter.

BRIEF DESCRIPTION OF THE INVENTION

A genetically modified vertebrate is provided that has an enhanced sense due to an overexpression of a predetermined odorant receptor. The vertebrate is genetically modified by introduction of DNA that comprises at least four sequential repeats of a sequence whose primary structure is at least 90% homologous with ACATAACTTTTTAATGAGTCT (SEQ ID NO: 1). The DNA causes a nearby odorant receptor coding sequence to be over represented in a singular gene choice fashion relative to a corresponding vertebrate that lacks the DNA.

In a first embodiment, a method of producing a genetically modified non-human vertebrate is provided. The method comprises inserting DNA into a genome of a non-human vertebrate using a vector. The vector comprises a M71 odorant receptor (OR) transgene backbone; at least three sequential repeats of a DNA sequence with two complete ds B-DNA turns, the DNA sequence being at least 90% homologous with 5' ACATAACTTTTTAATGAGTCT 3' (SEQ ID NO: 1); a transcription start site (TSS) disposed downstream of the at least three sequential repeats; an odorant receptor coding sequence disposed downstream of the transcription start site, the odorant receptor coding sequence coding for a predetermined odorant receptor; wherein the non-human vertebrate, after the step of inserting, develops a main olfactory epithelium (MOE) comprising multiple olfactory sensory neurons (OSNs), wherein between 10% and 95% of the OSNs express the predetermined odorant receptor.

In a second embodiment, a vector for genetically modifying a vertebrate is provided. The vector comprises a M71 odorant receptor (OR) transgene backbone; at least three sequential repeats of a DNA sequence that is at least 90% homologous with 5' ACATAACTTTTTAATGAGTCT 3' (SEQ ID NO: 1); a transcription start site (TSS) disposed downstream of the at least three sequential repeats; an odorant receptor coding sequence disposed downstream of the transcription start site, the odorant receptor coding sequence coding for a predetermined odorant receptor; wherein the vertebrate develops an olfactory epithelium that expresses between 10% and 70% of the predetermined odorant receptor.

In a third embodiment, a genetically modified non-human vertebrate is provided. The vertebrate comprises germ cells and somatic cells that contain an insertion of DNA within a 10 kb proximity of a transcription start site (TSS) of an odorant receptor transgene, such that the insertion causes the vertebrate to over represent a predetermined odorant receptor corresponding to the odorant receptor transgene relative to a corresponding vertebrate that lacks the insertion, wherein the DNA comprises at least three sequential repeats of a DNA sequence with two complete ds B-DNA turns whose primary structure is at least 90% homologous with ACATAACTTTTTAATGAGTCT (SEQ ID NO: 1).

In a fourth embodiment, a method of high-throughput screening for an odorant ligand is provided. The method comprising steps of: exposing a candidate odorant ligand to an olfactory neuron or cilia of a biosensor, the biosensor comprising a plurality of cells with neurons in an olfactory epithelium wherein greater than 1% of the neurons in the olfactory epithelium are expressing an odorant receptor (OR) through a singular gene choice enhancer nucleotide sequence with at least three repeats of a DNA sequence that is at least 90% homologous with 5' ACATAACTTTTTAAT-GAGTCT 3', the at least three repeats being disposed within 10 kb from a predetermined odorant receptor; and monitoring the olfactory neuron or the cilia for a change in expression of GDP, cAMP and/or ATP, wherein an increase corresponds to successful binding of the candidate odorant ligand to the predetermined odorant receptor.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 2A to 2C depict odor response profiles of in vivo Glomerular Imaging of M71 biosensors with 4•M71Cα lines, wherein

DETAILED DESCRIPTION OF THE INVENTION

This disclosure pertains to a method of controlling the expression of specific odorant receptors in vivo in mice by multimerizing a specific 21 bp sequence encompassing the homeodomain binding site sequence, TAATGA, known to be a determinant in OR gene choice and adding it to the M71 odorant receptor (OR) transgene backbone (see Rothman et al. The Promoter of the mouse odorant receptor gene M71; Mol. Cell. Neurosci. 28, 535-546, 2005). Of note, the 21 bp sequence was chosen to reflect two complete turns of double stranded B-DNA (10.5 bp per turn on average). The method reproducibly and dramatically increases the total number of olfactory sensory neurons (OSNs) expressing specific mouse or human OR coding sequences in different transgenic animals. The transgenic vector was designed in such way that any odorant receptor or G-protein-coupled receptors (GPCR) (human, mouse or from any species), can be shuttled into the transgenic backbone. Importantly, proof of concept studies show that transgenic mice with over-represented ORs show an increased sensitivity to cognate odors in odor detection behavioral tasks. As such, a versatile platform has been created that provides biosensors by genetically manipulating gene expression in the mouse's nose with great translational potential. The platform permits researches to study gene choice, axon identity and odor coding simultaneously in vivo, three processes that cannot be studied independently from each other.

To up-regulate the neuronal population expressing a given OR a method that generates transgenic mice in which 10-70% of the mouse olfactory epithelium expresses the same OR that has been labeled with a red fluorescent protein. An expression system was developed using the M71 (a mouse OR) transgene backbone containing a strong tunable enhancer placed upstream of any OR coding region. The tunable enhancer consists of repeats of a specific 21-mer sequence (hereafter referred to as ×21): 5' ACATAACTTTT-TAATGAGTCT 3' (SEQ ID NO: 1). This sequence contains the TAATGA sequence, which is correlated with singular gene choice events. Usually one OSN expresses only one OR. Once a given OSN has 'chosen' its OR the OSN does not choose another OR. Using the disclosed method, a given OSN system is forced to choose a predetermined OR of interest with greater probability.

Biosensors expressing the mouse M71 OR and the human OR1A1 OR have been validated, both on a molecular level and a functional level. Without use of the disclosed method about 0.1% of the total number of olfactory sensory neurons in the main olfactory epithelium express the same odorant receptor (OR) in a singular fashion and their axons coalesce into homotypic glomeruli in the olfactory bulb. In proof-of-principle studies the expression of a mouse OR (M71) has been increased by 45-fold (about 1-2%) to 100,000-200,000 OSNs and a human OR (OR1A1) has been increased by 500-fold (about 13%) to 1.3 million OSNs, while conserving the biological properties of the olfactory system. The transgenic animals have enhanced brain activity to known odors recognized by those specific ORs, as shown by live animal in vivo imaging. Importantly, improved odor detection seems to translate to the higher cortical regions, since the transgenic animals show increased sensitivity to their cognate odors in behavioral odor avoidance assays.

Downstream of the OR coding sequence an internal ribosomal entry site (IRES) is inserted followed by the coding sequence for a red fluorescent protein (tauCherry). This allows for bicistronic translation and, as such, co-expression of the OR of interest with tau-Cherry, enabling visualization of the over represented ORs in vivo using fluorescence microscopy. In one embodiment, the fluorescent protein is omitted when visualization is not desired.

Detailed Results

OR genes form the largest multigene family in mammals with about 1200 members in the mouse and about 350 members in humans. The main olfactory epithelium (MOE) expresses ORs through a poorly understood singular gene choice mechanism whereby only one allele of any odorant receptor gene is selected for specific expression in a given neuron. Axons from OSNs that express identical ORs coalesce into two out of the ~1800 glomeruli in the olfactory bulb (OB). The odorant receptor coding sequence (OR CDS) plays a role in the maintenance of gene choice. If the OR is not capable for this maintenance, then a second OR allele is tested for functionality. Hence, deletion of an OR CDS precludes the convergence of axons into a specific glomerulus and results in OSNs choosing to express other OR genes projecting to a variety of glomeruli in the OB. In addition, OR proteins are necessary for promoting axon guidance, axon identity and stabilizing neurons that have chosen to express those ORs. Finally, the OR protein needs to be targeted to the olfactory cilia where it will function in odor signal transduction. As used in this specification, the term odorant receptor coding sequence (OR CDS) refers to a sequence of DNA that promotes the growth of an individual odorant receptor.

In the case of a M71 OR minigene, a 7.5 kb DNA fragment accurately recapitulates the functionality of the gene-targeted M71 locus and imparts an expression pattern paralleling that of endogenous genes. Two highly conserved sequences were identified: (1) a single candidate O/E binding site and (2) a two candidate-Lhx2 homeodomain (HD) binding sites within this 161 bp region. An HD sequence is believed to be highly desirable for regulating the probability for any OR gene to be expressed.

Further analysis of sequences known to strongly influence OR gene choice such as the mouse H (the Homology region that activates the MOR28 cluster, and P (a sequence with high homology to the P3 minimal promoter, elements have revealed a set of three HD binding sites in close proximity to each other, and an associated O/E site, with one of the HD sites sharing the same 13 mer AACTTTTTAATGA (SEQ ID NO: 2) between them. When a 19 mer (see SEQ ID NO: 10, FIG. 1) containing this 13 mer sequence from P element was multimerized nine times (9×19) and placed upstream of the MOR23 transgene backbone, inconsistent increases in cell numbers were observed.

The disclosed enhancer was designed to accommodate two full turns of the double helix using a multimerized 21 bp HD encompassing 13 mer sequence from the "H element" resulting in a radical and reliable increase in expression of any odorant receptor protein in the context of the M71 transgene backbone. The disclosed method permits researchers, for the first time, to study OR gene choice, axon identity and odor coding simultaneously in its intact in vivo environment.

The Transgene

The effect of a multimerized 21-mer of the H element (DNA turns every 10.5 bp thereby allowing for maximum cooperativity) was tested on the probability of choice for any OR CDS expressed from the M71 transgene. Using the M71 transgene backbone including 485 bp of the M71 promoter upstream of the transcription start site (TSS) (FIG. 1), a modular version of the transgenic vector was created such that any number of 21 mer repeats can be shuttled into the NheI site at position −485. The modular version of the transgenic vector is a modified form of the M71 7.5 kb minigene disclosed by Rothman (The Promoter of the mouse odorant receptor gene M71; Mol. Cell. Neurosci. 28, 535-546, 2005) wherein the M71 OR CDS has been replaced with an OR CDS of choice. The transgene backbone refers to the disclosed minigene without the M71 OR CDS.

Any OR CDS of interest can be cloned into the AscI site followed by, if desired, a label such as an IRES-tauCherry cassette. The internal ribosomal entry site (IRES) allows for bicistronic translation and simultaneous expression of tauCherry enabling the visualization of the olfactory neuronal morphology.

Figure 1:
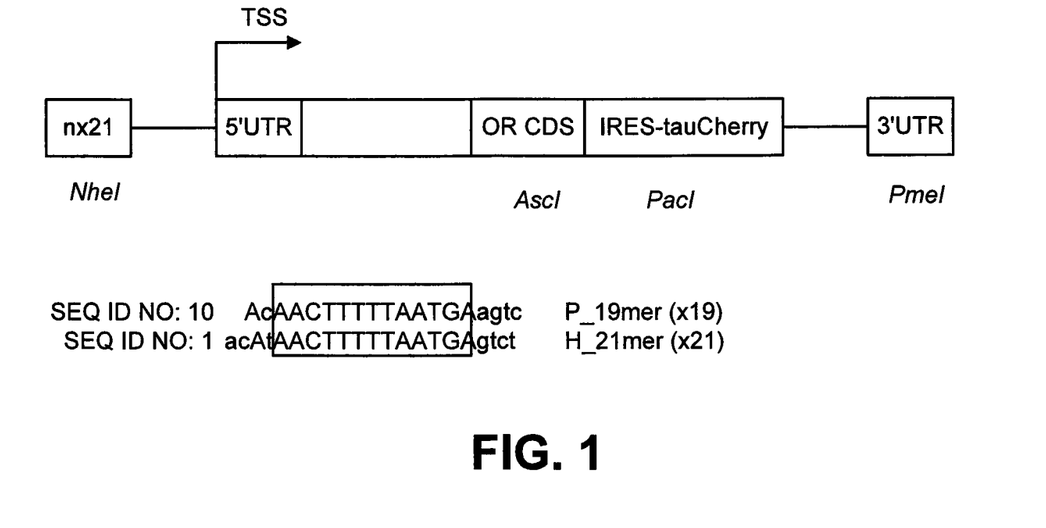
FIG. 1 depicts a design for a transgene using the disclosed DNA sequence.

FIG. 1 specifically depicts a design of a transgene. The transgenic vector was created using the M71 OR genomic backbone. Any number of H_21 mer (×21) repeats can be shuttled in the NheI site upstream of the TSS and any OR CDS can be cloned into the AscI site. An IRES-tauCherry cassette (Pad) follows the OR CDS. The internal ribosomal entry sequence (IRES) allows for bicistronic translation and simultaneous expression of mCherry enabling the visualization of the olfactory morphology. Transgenic animals were generated by pronuclear injection of PmeI (black) digested DNA. In one embodiment the repeats are disposed within 10 kb of a predetermined OR CDS. In another embodiment, the repeats are disposed at least 500 bp from a predetermined OR CDS but less than 10 kb from the predetermined OR CDS. In one embodiment the repeats are disposed upstream of the OR CDS. In another embodiment, the repeats are disposed downstream of the OR CDS.

Effect of 21 Mer Multimerization

An initial analysis of various M71 transgenic lines containing 0, 1, 2, 3 or 4 multimers of the 21 mer sequence was performed (Table 1).

| OR | Enhancer | Founds with OSN expression[1]/Germline with OSN expression | Robust OSN Expression[2] | Established germline mouse line |
|---|---|---|---|---|
| Mouse Odorant Receptors | | | | |
| M71 | 0x21 | 0.14[3]/1:2 | NO | NA |
| M71 D205E | 1x21 | NA/0:1 | NO | NA |
| M71-D205L | 2x21 | NA/2:3 | NO | NA |
| M71-D205N | 3x21 | NA/1:1 | NO | NA |
| M71 | 4x21 | NA/3:3 | YES | 4•M71Cα 4•M71Cβ |

-continued

| OR | Enhancer | Founds with OSN expression[1]/Germline with OSN expression | Robust OSN Expression[2] | Established germline mouse line |
|---|---|---|---|---|
| M71 | 5x21 | 6:6/1:1 | YES | 5•M71Cα |
| MOR122-2 | 5x21 | NA/5:5 | YES | 5•MOR122-2Cα |
|  |  |  |  | 5•MOR122-2Cβ |
|  |  |  |  | 5•MOR122-2Cδ |
| Human Odorant Receptors | | | | |
| OR1A1 | 5x21 | NA/2:2 | Yes | 5•OR1A1Cβ |
|  |  |  |  | 5•OR1A1Cδ |

[1]Positive Founders at 20 months of age
[2]Presence of stable glomeruli that are bigger than 30 μm (M71-IRES-tauGFP glomeruli)
[3]Small glomeruli are unstable in older animals.

This data shows that less than 50% germline animals containing fewer than four 21 multimers show expression of the cloned OR and none of them are robust expressers. On the contrary, 4×21 M71 lines generated robust expression in 100% of germline animals (3/3). Two 4×21-M71 lines (4•M71Cα and β) were bred for further analysis. In addition, the copy number of the transgenes insertions were assessed to determine influences the rate of OR expression by quantitative real-time PCR (qPCR) and found no correlation between the expression level and copy number. Hemizygous 4•M71Cα contain about 15 copies whereas hemizygous 4•M71Cβ showed about 24 copies. Interestingly, nine 0•M71C founders contained between 5-32 insertions of the transgene, but do not show any robust OR expression. Without wishing to be bound to any particular theory, it is believe the 4×21 enhancer is able to modulate the chromatin environment and as such promotes OR expression when randomly inserted in the genome.

Singular Gene Expression in the 4•M71Cα Line

In the 4•M71Cα line, the increase of OSNs expressing the M71 OR results in the coalescence of labeled axons onto one lateral glomerulus and one medial glomerulus per OB. Surprisingly, these glomeruli were significantly larger (300 μm) than typical glomeruli, providing the unique opportunity to answer a long-standing question in the field of olfaction: What is the effect of increasing axonal input to a single glomerulus on odor responses and behavior? To contrast the effect of increasing choice of the M71 OR in the 4•M71Cα line on the expression level of the "endogenous" M71 OR and on axon guidance and identity, this line was crossed to M71-IRES-tauGFP mice, gene-targeted at the M71 locus (M71G, 129 strain). A new mouse line was established that is either homozygous for M71G (M71G−/−, henceforth known as WT) or both homozygous for M71G and hemizygous or homozygous for the M71-IRES-tauCherry transgene (4•M71Cα−/0 or −/−; M71G−/− henceforth known as 4•M71Cα Hemi or Homo). Using coronal cryosections of the MOE of these 4•M71Cα hemi animals a total of 4754 mCherry-positive cells were counted expressing the M71 4×21 transgene and 221 GFP-positive cells; none of the red cells co-express the green marker in the MOE, suggesting that this 4×21 M71 transgene maintains monogenic expression. In addition, confocal imaging of the OB of these animals reveals co-convergence of mCherry-positive and endogenous GFP-positive axons onto the same isotypic M71 glomerulus, showing that OSNs expressing the M71 transgene have the same axonal identity as endogenous M71 OSNs. Axonal identity strictly correlates with the most abundant OR expressed in an OSN, thus it is unlikely that other ORs are enriched in 4•M71Cα OSNs. Moreover, it is unlikely that the level of M71 RNA transcripts is elevated in the 4•M71Cα OSN as they coalesce with M71G axons; this is consistent with previous observations that axons of OSNs expressing MOR23 from the 9×19 transgene co-converge into the same glomeruli as axons of OSNs expressing MOR23 from the endogenous locus and the knowledge that subtle changes to OR levels have dramatic affects on axon identity.

In Vivo Synaptophluorin (SpH) Imaging Of Glomerular Activity

Because the M71 OR is dorsally expressed in the olfactory bulb, any cloned OR using the M71 transgenic backbone will coalesce its axons onto dorsally located glomeruli, which makes them accessible for optical imaging. Optical imaging was therefore used to functionally characterize transgenic M71 projections in the OB. To examine their functional properties odor-evoked activity was imaged from the OBs of mice expressing the genetically encoded activity reporter SpH in all mature OSNs. Simultaneously recordings were obtained from mice that are either hemizygous or homozygous for 4•M71Cα (gene-targeted M71-GFP is out crossed) and heterozygous for SpH and identify red M71 glomeruli. Seven different M71-selective ligands were used from ex vivo analysis of genetically defined M71 OSNs in gene-targeted mice: three of these ligands produced responses by SpH imaging: Acetophenone (ACP), 4-methyl acetophenone (4MACP) and 2,4-dimethyl acetophenone (24dMACP) when delivered at different odor dilutions varying between 0% and 15%. The maximum change in fluorescence $[(dF/F)_{max}]$ per odor concentration was calculated for each compound over a 14 s trial period having a pre-odor (3 s), odor (4 s) and post-odor (4 s) acquisition. dF/F values for all glomeruli were calculated with a standardized 50 μm window, which is fully contained in all imaged glomeruli of both hemi and homo 4•M71Cα animals. (FIG. 2A, FIG. 2B and FIG. 2C: Each data point represents the average (dF/F). of 4-16 glomeruli imaged). Triangles indicated responses from hemizygous animals, circles indicate homozygous animals and asterisks indicate homozygous responses that are significantly higher than hemizygous response when the animals are presented with the same odor concentration. All imaged mice are heterozygous for omp-SpH.

M71 ligands show the same efficacy but different apparent affinity in hemizygous 4•M71Cα animals. In hemizygous animals, the average highest $(dF/F)_{max}$ is 3.49% for ACP is (n=6 at 1.77 uM), 4.48% for 4MACP (n=9 at 0.69 uM) and 4.15% for 24dMACP (n=7 at 0.66 uM). These results show that all three compounds cause a similar efficacy [maximum response obtained by a compound, i.e. average $(dF/F)_{max}$] in terms of M71 OR activation (A one-way ANOVA comparing the highest $(dF/F)_{max}$ values between Hemi animals did not reveal any significant differences). However, the apparent affinity of the M71 OR for 4MACP and 24dMACP is significantly higher than ACP since the latter two compounds start activating the M71 glomerulus at a lower concentration (FIG. 2). For example, when delivered at the same concentration (i.e. ~0.70 uM), efficacy for ACP is 0.73% (n=4). This is significantly lower than the efficacy for both 4MACP (4.48%, n=9, Student's t-test, p<0.0001) and 24dMACP (4.15%, n=7, Student's t-test, p<0.0001). Hence, similar odor efficacy is observed at lower concentration for both 4MACP and 24dMACP when compared to ACP responses in the Hemi animals.

Figure 2A:
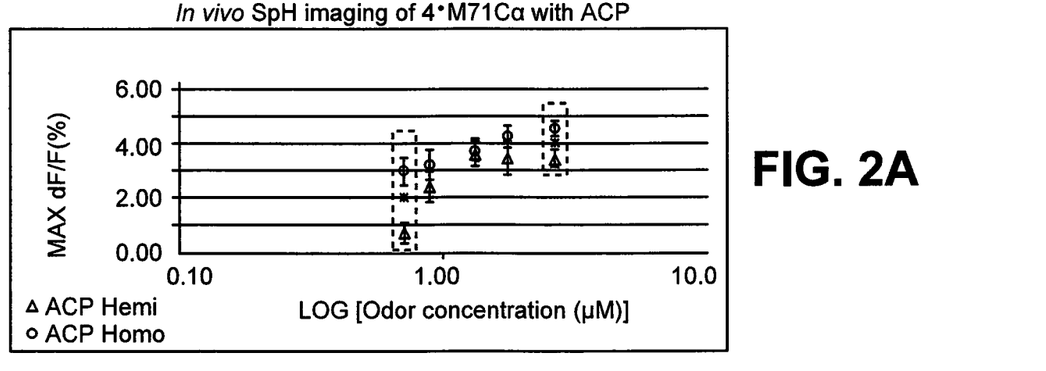
FIG. 2A shows acetophenone (ACP)
Figure 2B:
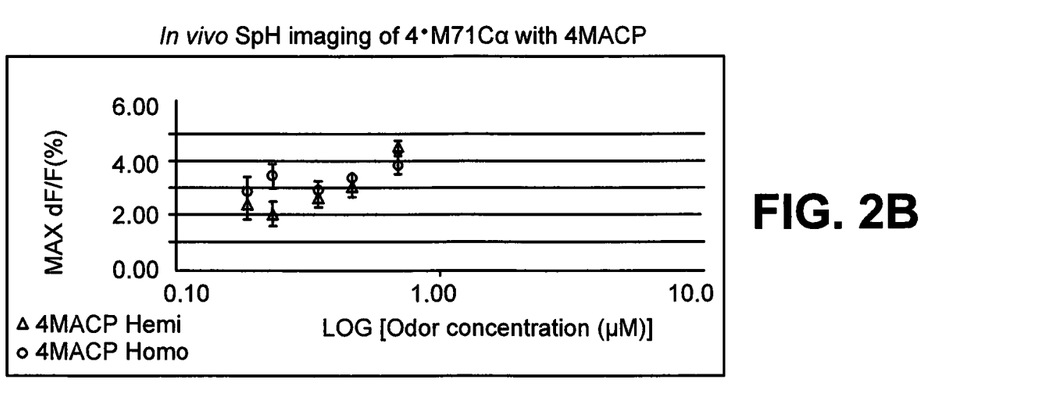
FIG. 2B shows 4-methyl acetophenone (4MACP) and FIG. 2C shows 2,4-dimethyl acetophenone (24dMACP)
Figure 2C:
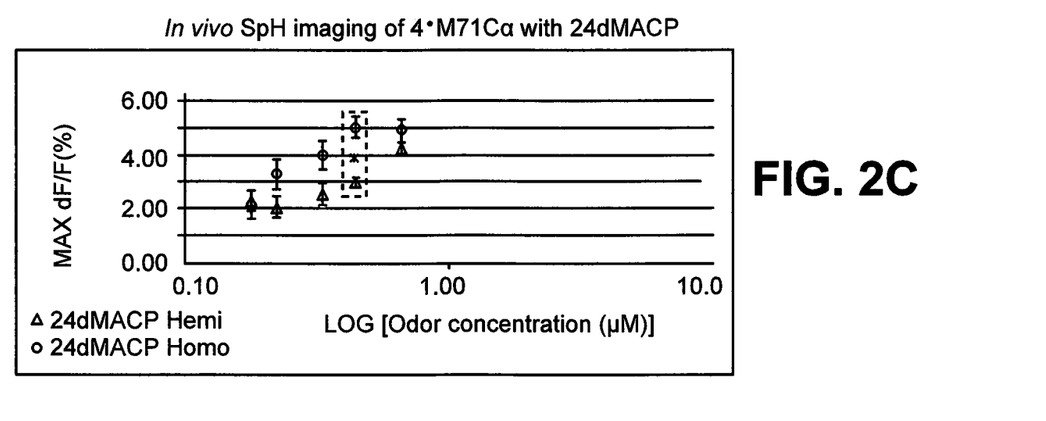

Doubling the number of OSNs expressing M71 changes the efficacy for both high- and low-affinity ligands. In homozygous animals, the highest efficacy for ACP is 4.57% (n=14 at 2.66 uM), 3.82% for 4MACP (n=16 at 0.69 uM) and 4.92% for 24dMACP (n=7 at 0.46 uM). When comparing hemizygous and homozygous animals, the dose-responses do not differ significantly for 4MACP. For 24dMACP, however, a significant increase in efficacy was observed at 0.44 uM (2.92% (n=4) vs. 4.92% (n=7), Student's t-test, p=0.0075), suggesting that doubling the number of OSNs that choose to express M71 changes the efficacy of this ligand when presented at this particular concentration. In addition, the average efficacy (of all concentrations and odors) is significantly different between 24dMACP and 4MACP in homozygous animals (4.92% vs 3.83%, Student's t-test, p=0.0272), even though they show practically the same dose-response in the hemizygous animals (FIGS. 2A-2C). Doubling the number of neurons expressing the M71 OR changes the efficacy of 24dMACP, thus empirically identifying it as the higher-affinity ligand.

Interestingly, in the homozygous animals, when ACP is delivered at 0.71 uM, the efficacy is 3.00% (n=6) which is significantly higher (Student's t-test, p=0.0189) than the response at the same concentration in the hemizygous animals (0.73%, n=4)), reflecting a change in apparent affinity for this ligand. Moreover, at the highest ACP concentration delivered (i.e. 2.66 uM), the homozygous response is also significantly higher than the heterozygous response (4.57%, n=14 vs. 3.46%, n=9).

Given a defined number of OSNs expressing M71, saturation of the glomerular response is reached at certain concentrations of a given odor. However, this saturation response is not determined by a specific subset of OSNs expressing one OR type. The data show that doubling the number of neurons expressing M71 can increase the glomerular efficacy at specific concentrations.

Ex Vivo Vs. In Vivo Ligand Profiling

In the proof of concept experiments, odors are delivered from the headspace of odor saturator vials containing 99% pure odorants and flow-diluted with air ($N_2$) prior to delivery to the anesthetized animal. The molar vapor concentration (uM) reaching the animal's nose is therefore determined by odorant saturated vapor pressure ($P_s$), which can differ dramatically between odorants. For example, 15% air dilution of ACP ($P_s$=0.3260 mmHg at 25° C.) generates 2.66 uM air concentration, while 4MACP and 24dMACP ($P_s$=0.0849 and 0.0811, respectively) are delivered at 0.69 uM and 0.66 uM, respectively. In vivo responses were compared with previous in ex vivo data by analyzing seven different odors that did (benzaldehyde, ethylmalthol, 2 amino acetophenone, ACP, 4-metoxyacetophenone, 4MACP and 24dMACP) or did not (methylbenzoate and menthone) elicit a M71 response through ex vivo patch clamping of dendritic knobs when delivered in liquid phase. Glomerular activity was only observed with ACP, 4MACP and 24dMACP. There are two reasons for these findings: (1) the odor is not delivered at a high enough concentration and/or (2) the odor may not generate a high enough activation within OSNs. The minimal $P_s$ necessary to be able to elicit a response in vivo is found to be 0.0811 mmHg (which is the $P_s$ of 24dMACP). 4-metoxyacetophenone (a high responder ex vivo), does not show glomerular activation in our hands and has $P_s$=0.0133 (<0.0811) mmHg, nor does benzaldehyde (a low responder ex vivo), which has the highest $P_s$ of all odors tested (1.0100 mmHg at 25° C.). Hence it is suggested that, when the minimal $P_s$ requirement is met, a minimum current amplitude (pA) M71 response (ex vivo) is used for an odor to activate glomeruli in the SpH imaging setup.

Odor Detection Threshold in a Two-Bottle Discrimination Behavioral Task

Sensitivity studies performed in Wistar rat neonates and adults have shown that the highest sensitivity to an odor (lowest threshold) correlates with the highest OSN density in the MOE. Even though the total number of mature OSNs in the 4•M71Cα animals were not changed [qPCR shows that olfactory marker protein (omp) RNA levels are not changed between 4•M71Cα and WT animals], the neuronal representation of OSNs expressing M71 is increased. Therefore, it was desirable to assess whether detection of the most robust M71 ligand is amplified in this M71 line. An avoidance task was used in which the odorant 24dMACP is added to drinking water and becomes an aversive stimulus associated with injection of Lithium Chloride (LiCl), a compound known to induce gastric malaise. After conditioning homozygous 4•M71Cα animals and their WT littermates to water containing a 10-4 dilution of 24dMACP, the animals are given the choice between plain water and water with decreasing concentrations of 24dMACP ($10^{-4}$, $10^{-6}$, $5\times10^{-7}$ and $10^{-7}$). Note that all tested animals are homozygous for M71G, so even WT have a functional M71 OR.

Figure 3A:
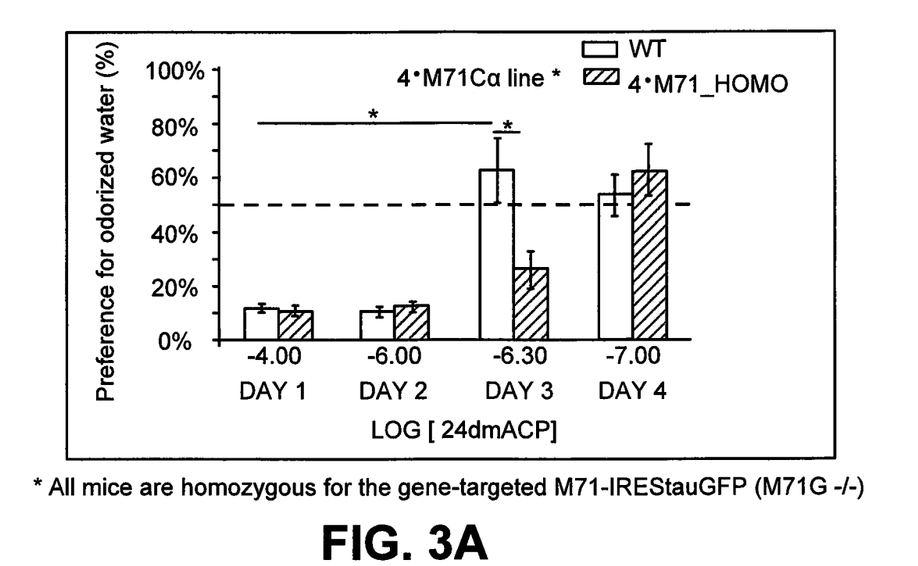
FIGS. 3A, 3B and 3C are graphs depicting the results of behavior avoidance assays on 4•M71Cα homo lines with 2,4-dimethyl acetophenone (24dMACP) (FIG. 3A); 5•M71Cα lines with 2,4-dimethyl acetophenonen (24dMACP) (FIG. 3B) and 5•OR1A1Cβ lines with (−)-Carvone (FIG. 3C).

The results are presented as a preference index (PI) for the odorized water for each group of animals which is calculated as the amount of the odorized water consumed divided by the total amount of liquid (odor and no-odor water) consumed over a 24 hr time period (FIG. 3A). A PI of 50% reflects no preference of the animal. A $10^{-4}$ dilution of 24dMACP corresponds to 646 μM, a concentration that can be easily detected by both homozygous and WT animals and does not cause an aversive response by itself (the PIs for drinking water containing $10^{-6}$ of 24dMACP for naïve, unconditioned mice are as follows: WT: 60%+/−7.72 (n=5) and Homo: 59%.+/−1.94 (n=5)). When presented with $10^{-4}$ and $10^{-6}$ dilutions, both conditioned 4•M71Cα homo and WT animals show a clear aversion towards 24dMACP reflected through an average PI for 24dMACP of about 10%. However, when 24dMACP is delivered at $10^{-7}$ all animals fail to detect the presence of the odor with an average PI of 53.41% for the WT (n=4) and 62.67% for the homozygous animals (n=8). This suggested that if the sensitivity of these M71 MouSensors were changed, the threshold would be between $10^{-6}$ and $10^{-7}$. Indeed, the PI of the WT group is significantly higher than the PI of the mutants at dilution $5\times10^{-7}$ (62.79% vs 26.12%, Student's t-test, p<0.05), suggesting that while the WT fail to detect the odor at $5\times10^{-7}$, the mutants still show aversion behavior and thus still smell 24dMACP. Importantly, even the WT animals show a lower PI for the odorized water at $10^{-4}$ than at $5\times10^{-7}$ (11.84% vs 62.79%, Student's t-test, p<0.05), indicating that the behavioral difference is most likely a result of the increased ability of the mutants to detect the odor rather than a learning deficiency in the WT.

To compare specific odorant sensitivity between the 5•M71Cα and the 4•M71Cα line, the 2-bottle discrimination behavioral task was performed with 24dMACP as described above (FIG. 3B). In summary, at dilution $5 \times 10^{-7}$ the average PI of the 5•M71Cα group (n=9) is 19.62%, which is significantly (p<0.01) lower than the PI of the WT group (n=8; 55.32%). Even though the same but slightly more significant 0.3 log decrease in odorant detection threshold is observed in the 5•M71Cα line, it is important to mention that 5•M71Cα hemi animals were used which have about 1.6% of their OSNs expressing M71 (similar to the 4•M71Cα homo animals with about 2% M71 expressing OSNs).

It is important to note that precise odor-thresholding based on number of OSNs is not being performed.

M71 Mousensors do not have a Monoclonal Nose

The percentage of OSNs expressing M71 changed in our 4•M71Cα line (which is also homozygous for M71G) was assessed. Using qPCR, the level of M71-mCherry RNA was found to be significantly increased by about 12 fold (Student's t-test, p<0.01) when compared to M71-GFP within the hemizygous 4•M71Cα line and by about 45 fold (Student's t-test, p<0.01) when compared to M71-GFP in the WT (M71G−/−) line. This apparent discrepancy is explained by the fact that the expression of the gene-targeted M71-GFP is 3.89 fold higher in the 4•M71Cα Hemi animals when compared to the WT animals (Student's t-test, p<0.01). These numbers suggest that increasing M71-mCherry RNA levels help stabilize the endogenous M71-GFP RNA levels early in development in the 4•M71Cα line, instead of cannibalizing them, leading to an increase in endogenous M71 transcripts in the 4•M71Cα animals. This model is supported by the fact that olfactory neurons are interdependent in maintaining axonal projections. In addition, the postsynaptic bulbar circuitry necessary to convey olfactory sensory information to the higher cortical regions remains intact, as glomerulus-like structures may form in absence of postsynaptic olfactory neurons. An existing YFP-g transgenic mouse line (in which 30% of the postsynaptic mitral cells are labeled in yellow) was crossed to the 4•M71Cα line to visualize mitral cell dendrites. Mitral cell innervation of the M71 glomerulus is normal, as dendrites from postsynaptic mitral/tufted cells are present.

The M71G allele is expressed in about 0.03-0.06% of the OSNs (about 3K OSNs in 5-10M total, i.e. lower than the average 0.1%. Therefore, the above observations suggest that the 4•M71Cα Homo animals (used in the behavior) have about 1-2% of OSNs expressing the M71 OR. In this regard, the animals are fundamentally different from other animals generated by altering the neural representation of odors by decreasing expression of most ORs by 95% and replacing them with M71, creating animals with a monoclonal nose. Despite previous observation that most OSNs and glomeruli can be (weakly) activated by ACP, odor discrimination and performance in associative learning tasks is impaired in these animals. One possible explanation for this behavior is that broad uniform activation (such as in the monoclonal nose) may cause lateral inhibition through intricate feedback mechanisms (at the level of detection and/or perception) and ACP may be detected as olfactory "noise". In this regard, many small glomeruli could be disadvantageous compared to fewer very large glomeruli (which are observed in our 4•M71Cα line) and patterned activation may be necessary for signal detection. On the other hand, by reducing the representation of endogenous OR genes by 20-fold, they may have ablated the high-affinity OR for ACP as well. (e.g. Olfr145, von der Weid et al., Nature Neuroscience, Large-scale transcriptional profiling of chemosensory neurons identifies receptor-ligand pairs in vivo, 2015)

A Versatile Platform

The phrase "odorant receptor coding sequence" refers to G-Protein Coupled Receptor (GPCR) that exhibits the following functions (1) odorant identification and olfactory signal transduction (2) maintenance of first choice to block the expression of a second OR (3) promotion of maturation of the neuron (4) providing the axons with the ability to grow and (5) encryption of axonal identity to growing axons. Numerous examples of odorant receptor transgenes are known to those skilled in the art with M71 and OR1A1 merely being two examples. The disclosed methods are applicable to a wide range of odorant receptor transgenes.

To assess the effect of further increasing the number of multimers as a ubiquitous enhancer on the number of OSNs choosing to express any cloned OR, lines containing 5×21 enhancers for two mouse ORs, M71 and MOR122-2 were created. All founders for 5•M71C (6/6) and one germline animal 5•M71Cα show high levels of M71 expression (Table 1) and form glomeruli in the bulb. In addition, all five germline animals for 5•MOR122-2 show high levels of expression for MOR122-2. Moreover, when comparing 5•M71Cα with 4•M71Cα, the data show adding an extra 21 mer increases the number of OSNs expressing the M71. This increased number appears to be a result of multimerization and not of increased copy number of the transgene in the genome (about 16 times for 5×21 M71 vs. about 15 for the 4×21 M71 transgene. In addition, using coronal cryosections of the MOE of a 6.5 weeks old 5•M71C Hemi animal a total of 52 green cells were counted amongst a large population of red cells and none of them coexpressed. These data show that adding five 21 mers maintains singular gene expression in OSNs. Based on current models of singular gene choice, this choice enhancer can still be suppressed in a large number of neurons and should be a target of silencing in non-cherry cells. This disclosure provides a model system for testing the role coding sequences or other genomic sequences for its capacity to be silenced.

Figure 3B:
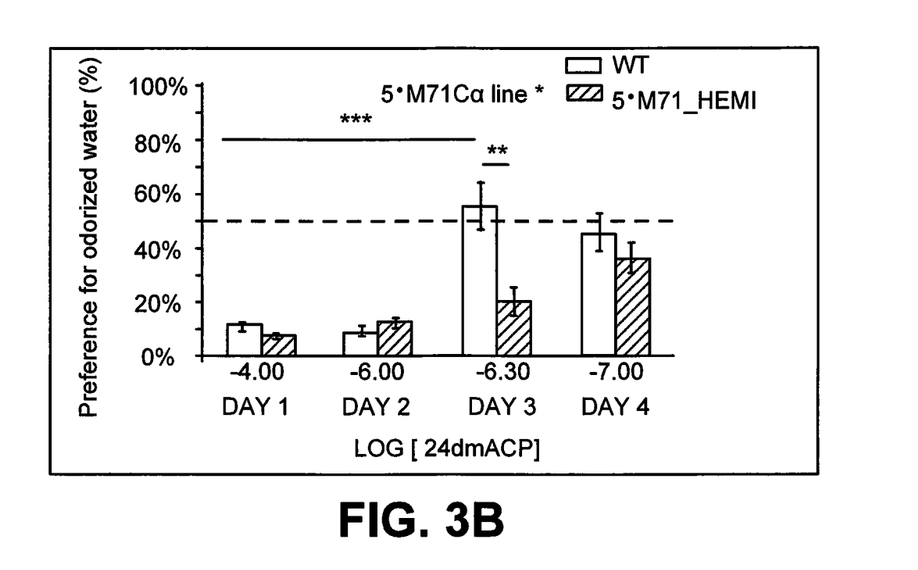
Figure 3C:
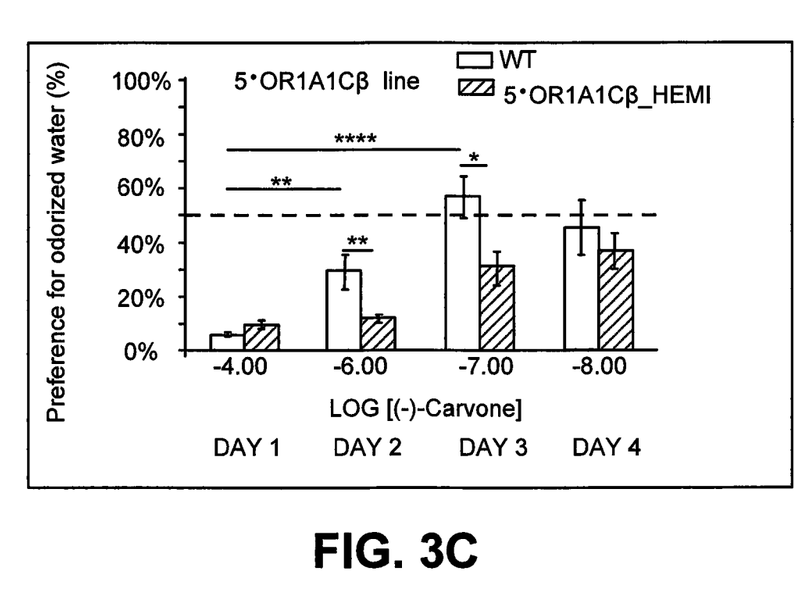

To further evaluate the versatility of this platform, the probability of choice of expression of a human OR was increased by cloning OR1A1 into the 5×21 M71 transgenic backbone. Both germline animals (5•OR1A1Cβ and δ) show robust expression of the human OR1A1 receptor in the MOE and stable glomerular formation in the OB. qPCR reveals even a ~12 fold increase of OR1A1 RNA in the 5•OR1A1Cβ hemi animals when compared to the M71 RNA levels in the 4•M71Cα hemi line. Again omp levels were not changed. Clearly, the representation of some ORs must be decreased to explain this equilibrium. In the 4•M71Cα homo animals, a mere 2-log increase in M71 RNA levels leads to a detectable 0.3-log change in threshold. Therefore, without wishing to be bound to any particular theory, it is believed that further increases in the neuronal representation of specific ORs may decrease detection thresholds even more. However, a delicate balance must exist between cell number and sensitivity. This hypothesis was tested using the established two-bottle behavioral avoidance task with the 5•OR1A1Cβ mice (FIG. 3B). Conditioning of 5•OR1A1Cβ hemi animals (n=12) was performed and their WT littermates (n=7) to water containing a 10-4 dilution of (−)-Carvone, a known OR1A1 ligand. For four consecutive days, animals were given the choice between plain water and water with decreasing (10-4, 10-6, 10-7 and 10-8) dilutions of (−) Carvone (FIG. 3C). Both groups (WT and Hemi) show clear aversion towards a $10^{-4}$ dilution of (−)-Carvone (AVG PI WT=6.17% and AVG PI hemi=10.26%), reflecting successful conditioning. Both WT (AVG PI=55.52%) and Hemi (AVG PI=47.88%) cannot detect a $10^{-8}$ dilution of (−)-Carvone. At $10^{-6}$ and $10^{-7}$ however, there is a clear difference in detection between WT and Hemi ($10^{-6}$: AVG PI WT=27.65% vs. AVG PI Hemi=11.41, Student's T-test p<0.01 and $10^{-7}$: AVG PI WT=53.88% vs. AVG PI Hemi=30.24, Student's T-test p<0.05). Importantly, even the WT animals show significantly lower PIs for the odorized water at $10^{-4}$ than at $10^{-6}$ (6.17% vs. 27.65%, Student's t-test, p<0.01) and at $10^{-7}$ (6.17% vs. 53.88%, Student's t-test, p<0.0001), again indicating that the behavioral difference is most likely a result of the increased ability of the mutants to detect the odor rather than a learning deficiency in the WT (FIG. 3B). These findings indicate that expressing OR1A1 in about 40% of the OSNs translates into a 2-log difference in (−)-Carvone detection thresholds.

CONCLUSIONS

The disclosed transgenic platform is an invaluable tool to further study the mechanisms of singular gene choice and odor coding in the olfactory system. Mechanistically, HD binding motifs could modulate the probability of OR gene choice by attracting polymerase assembly factors, enhancing transcription initiation, or stabilizing transcription elongation. Placing HD elements in close proximity of each other will most likely favor strong cooperative binding of transcription factors. In this regard, nine 21mers have been multimerized resulting in even greater representation of ORs in the olfactory epithelium. In one embodiment, ten or fewer 21mers have been multimerized. This platform further enables one to dissect the mechanism of OR gene choice or negative feedback on first choice using mutant OR sequences. In addition, the possibility to express human ORs in large numbers of mouse OSNs using the disclosed technology provides a breakthrough in vivo approach to finally crack the olfactory code.

An example of a 5×21 annealed ultramer insertion into the NheI site (gctagc) is provided below. A forward ultramer comprising a five-repeat is given by ctagcACATAACTTTT-TAATGAGTCTACATAACTTTTTAA TGAGTCTACAT-AACTTTTTAATGAGTCTACATAACTTTTTAAT-GAGTCTACA TAACTTTTTAATGAGTCT (SEQ ID NO: 11). A reverse ultramer comprising a five repeat is given by ctagAGACTCATTAAAAAGTTATGTeAGACTCAT-TAAAAA GTTATGTAGACTCATTAAAAAGTTATGTA-GACTCATTAAAAAGTTATGTg (SEQ ID NO: 12).

A M71 promoter sequence (485 bp plus gctagc) is given by:

(SEQ ID NO: 13)
```
gctagcTCATGATGCATCATGGTGACTAGCTAACAATATGTAATAACCAT

CATGGCACTGAGAATGATGTTGCTGGTAGTTACTGTGGTGCCTATTGAGA

TGAAAATGACAATAATGATAATACATCAGTAGTAAAGGTGATAGCCATGG

TCATAATGGTAATGATGATAAGGATGGGTGGGTAGTGGTGATGGATGGTT

GGTGGTGGTGGTGGTGATGGTAGTGGTAGGGGGGTAATGGTGGTGGTAAC

GGCTCTGTTGATGCTAAATTGTTCATTGCCCCATTATATTCTAAGTTTCT

GAAACTGAAAGATGACTTTTACAGATAAAAGAAGAATTAACACACTTGGG

AAATAAAACATGATTCACAGAACAAGAGAAAACATGAACTAATTGTTACT

TTAGAGACAACAATGGTCTCTAGAGTGACTATATCCCAGGAGATGATCCA

CACACACACACACATATATATAAACAGAACCCCCAATTTTT.
```

The 5×21 M71 transgene promotor is given by (SEQ ID NO: 14)
```
gctagcACATAACTTTTTAATGAGTCTACATAACTTTTTAATGAGTCTAC

ATAACTTTTTAATGAGTCTACATAACTTTTTAATGAGTCTACATAACTTT

TTAATGAGTCTctagcTCATGATGCATCATGGTGACTAGCTAACAATATG

TAATAACCATCATGGCACTGAGAATGATGTTGCTGGTAGTTACTGTGGTG

CCTATTGAGATGAAAATGACAATAATGATAATACATCAGTAGTAAAGGTG

ATAGCCATGGTCATAATGGTAATGATGATAAGGATGGGTGGGTAGTGGTG

ATGGATGGTTGGTGGTGGTGGTGGTGATGGTAGTGGTAGGGGGGTAATGG

TGGTGGTAACGGCTCTGTTGATGCTAAATTGTTCATTGCCCCATTATATT

CTAAGTTTCTGAAACTGAAAGATGACTTTTACAGATAAAAGAAGAATTAA

CACACTTGGGAAATAAAACATGATTCACAGAACAAGAGAAAACATGAACT

AATTGTTACTTTAGAGACAACAATGGTCTCTAGAGTGACTATATCCCAGG

AGATGATCCACACACACACACACATATATATAAACAGAACCCCCAATTTT

T.
```

Method of High-Throughput Screening for an Odorant Ligand

Also disclosed in this specification to a method to measure biochemical changes in this OR signal transduction cascade within olfactory neurons when challenged with odors.

When odors bind odorant receptors (ORs), a signal transduction cascade ensues whereby the Golf alpha subunit becomes activated through binding to GTP. Subsequently, Golf-GTP activates adenylate cyclase III, which catalyzes a conversion of ATP into cAMP. The reaction terminates with the cleavage of GTP to GDP creating Golf-GDP.

Odorant receptors are notoriously hard to express in vitro. Because heterologous expression systems are lacking, most ORs remain orphans, meaning that their correspondent ligands are unknown. Thus, the olfactory code has to be studied in vivo, however this process is hampered because each OR gene is expressed in only 0.1% of the OSNs, making it difficult to correlate specific ligands to their cognate ORs.

One group claims to have found a way to express ORs in vitro using a chaperone molecule. Duke University licenses the use of this patented technology exclusively to ChemCom, a small Belgian company. (Saito et al., Cell, Vol. 119, 679-691, Nov. 24, 2004) Therefore, all big players in the fragrance industry have to find a "work around" to express ORs. Currently, research perfumers and human psychophysics empirically validate the odor quality of newly synthesized molecules. This expensive method is ineffective because less than 1% of the manufactured new molecules find their way to the market per year, largely due to the lack of a high-throughput screening platform that can reduce the number of candidate molecules to be tested by humans and ultimately reduce the pipeline cost.

The methods described elsewhere in this specification provide a platform that can express any odorant receptor, including human ORs, in large quantities in the mouse brain. The main olfactory epithelium that contains these transgenic OR expressing olfactory sensory neurons can be easily dissected and lysed.

ORs are G-protein coupled receptors (GPCR) that, when activated by their ligand, initiate a signaling pathway that involves the conversion GTP to GDP and ATP into cAMP.

Therefore, an increase in GDP/cAMP or a decrease in ATP is an indicator of ligand binding activity.

Because the biosensors described in this disclosure express the OR of interest in the majority of their cells any measurable increase in GDP/cAMP (or decrease in ATP) by a specific ligand reflects activation of the transgenic OR. The method described herein provides a quantitative measurement of increased GDP/cAMP decreased ATP after specific odorant activation as a means for high-throughput screening of scent molecules (agonists and antagonists) using any genetic platform that increases the neuronal representation of specific ORs.

Molecular kits that quantify these biochemical changes are commercially available. Levels of cAMP and ATP can be measured by existing technologies, such as luciferase kits or by direct coupling of ATP to Quenchers and/or fluorophores. In one embodiment, a microfluidic chip is used to measure activity.

Applications

One benefit of a genetic approach to create biosensors is that the increased sense of smell will be genetically defined and thus inheritable. For example, offspring of a TNT mouse will also carry the enhanced sensory ability. In addition, transgenic mice have fast breeding times and maturation rates; the gestation period for a mouse ranges from 18-22 days. Additionally, animals with an inherent enhanced sense for specific smells are anticipated to have dramatically decreased training time and enhanced the efficiency.

The disclosed methods are useful in multiple applications including disease diagnostics, drug prevention, search and rescue and pathogen detection.

Examples of biosensors useful in disease diagnostics include biosensors that identify tuberculosis (TB) in human saliva samples. Globally, the infectious disease TB is a leading cause of death, second only to AIDS. *M. tuberculosis*, the bacteria that causes TB, produces two specific odors (Methyl nicotinate and Methyl 4-anisate) which are unique to the bacteria. ORs sensitive to these odors can be identified and used in our transgenic platform to create TB biosensors.

Examples of drug prevention biosensors for contraband searches include cocaine sensitive biosensors. Examples of search and residue biosensors include biosensors that provide police assistance to help locate victims after natural disasters (e.g. cadaver dogs). Examples of biosensors for pathogen detection in livestock include biosensors that identify of animals infected with cattle virus.

Materials and Methods

Subjects: Mice used in this study were bred and maintained in the Laboratory Animal Facility of Hunter College, CUNY. The Hunter College IACUC approved all procedures. Animal care and procedures were in accordance with the *Guide for the Care and Use of Laboratory Animals* (NHHS Publication No. (NIH) 85-23).

Genotyping

Presence of 4X21-M71-IRES-tauCherry transgene was assessed by PCR by scoring for the mCherry gene with the following primers: FWD: 5' CCCTGGACAACATCACAC 3' (SEQ ID NO: 3) and REV 5' CCCTCCATGTGCACCTT-GAAGCGCA 3' (SEQ ID NO: 4). To distinguish between hemizygous and homozygous 4•M71Cα animals we used a qPCR method. Presence of the M71-IRES-tauGFP gene targeted allele was determined by using primers to detect GFP: FWD 5' CCCTGGACAACATCACAC 3' (SEQ ID NO: 3) and REV 5' CGTTTACGTCGCCGTCCAGCTC 3' (SEQ ID NO: 5) and primers to detect the WT M71 allele with FWD 5' CCGCACTGGACAAAACACTGAGGAG 3' (SEQ ID NO: 6) and REV 5 'CTGTTTCCTGTTC-AGAGTTGGGTG 3' (SEQ ID NO: 7), allowing us to distinguish between WT, Hemi and Homo animals.

Olfactometry: Odors (purchased form Sigma Aldrich) were delivered using a custom built olfactometer controlled by an Arduino board with custom shields operating Teflon solenoids (Neptune Research) and connected to two Mass Flow Controllers (Alicat Scientific, Inc) to dilute the clean air ($N_2$, max flow is 2 Lpm) and to dilute the odorized air (max flow is 300 SCCM). Nitrogen ($N_2$) was used as the vapor carrier to avoid oxidation. Odor concentrations are expressed a % dilutions of saturated vapor and as molar saturated vapor concentration (μM s.v.), calculated using published vapor pressures at 25° Celsius (US EPA, Estimation Programs Interface Suite, v 4.0. Flow diluted odors were delivered at 2 Lpm mixed prior to the delivery site with air odorized with varying dilutions of odorant taken from the saturated headspace of pre-cleaned amber vials with white polypropylene closures and septum (J. G. Finneran) containing 99% pure odorants. To avoid contamination of the olfactometer, odorized air was never passed through the Teflon valves. Instead, odors were mixed with $N_2$ in T-shaped mixing chambers (Neptune Research) and delivered to the animal's nose using an arduino controlled vacuum system. Odorized streams carrying different odors did not come into contact. Output of the olfactometer was calibrated using the tracer odor Pinene and a photoionization detector (PID; Aurora Scientific).

In vivo SpH Imaging: Mice were anesthetized using Ketamine (100 mg/kg)/Xylazin (5 mg/kg) and maintained with Isoflurane (2.5% in 02) and immobilized using a stereotactic head holding device (Narishige, Inc.). Optical signals for SpH and mCherry were recorded using an ANDOR Neo 5.5 sCMOS camera connected to a NIKON AZ100 epifluorescence microscope (NIS Elements) with a 4× objective (numerical aperture 0.4). Excitation wavelengths of 475 nm for SpH and 575 nm for mCherry and emission of 520 nm for SpH and 635 nm for mCherry were used to obtain images of the dorsolateral bulb through thinned skull overlaying the bulb of a freely breathing animal. Each imaging trial consisted of a pre-odor (3 s), odor (4 s) and post-odor (4 s) acquisition, with a total acquisition time per trial of 14 s (including 3 s of valve switch delay). Using serial code, the arduino controlling the olfactometer was integrated in the NIS Elements software, so that the entire image acquisition sequence and flow-diluted odor delivery is controlled by the microscope software.

Image Processing: Calculation of image response statistics was performed using custom code written in Matlab (Mathworks). Image frames were exported from the microscope NIS Elements AR Software and imported into Matlab. Frames were spatially bandpass filtered (Gaussian kernel; fspecial; high pass sigma=500 urn; low pass sigma=10 urn). Image frames were divided by the mean of the frames collected prior to odor onset (resting F) to correct for light distribution across the image. To generate glomerular activity maps (dF/F), divided pre-odor frames were subtracted from divided post odor frames. Regions of interest (ROIs) circles of radius 50 μm) were selected from manual examination of the post odor frames. Activity time-courses within each ROI were generated by averaging all pixels falling within the ROI for each frame. The resulting traces were exported into Excel for further analysis.

Olfactory behavior test: A two-bottle discrimination test was performed as previously described. Since the mice are tested for the ability to detect a single odor in drinking water at increasingly lower concentrations, this discrimination assay is also considered a detection threshold test. Mice 8 weeks old were individually housed and given food ad libitum but restricted access to saccharin-phthalic acid solution ($2.1\times10^{-2}$ M sodium saccharin and $10^{-3}$M phthalic acid pH 6.5) for 1 h twice a day for two days before the assay begins. This ensures mice would commence drinking the solution during the conditioning. On day 3 (conditioning day) mice are exposed to sodium saccharine phthalic acid (SSPA) solution with 1 dilution of odorized water for 10 minutes. Immediately after, they are injected with lithium chloride intraperitoneally (15 µl/g body weight of a 0.6 M solution) to induce the aversive malaise and lethargy state. After two hours mice are returned to their home cage and given access to two bottles of drinking water; they are given the choice between SSPA solution containing a $10^{-4}$ dilution of the odor versus the non-odorized SSPA solution. During the following 3 days, every 24 hours, the location of the bottles is reversed and the concentration of the odorized solution is decreased to $10^{-6}$, $10^{-7}$ and $0.5\times10^{-6}$, respectively. Every day both bottles are weighed to determine the amount of liquid consumed. A preference index was calculated as the amount of odorized solution consumed divided by the total amount of water solution consumed for each mouse for every 24 hour test period at each odor concentration. Student's t test was performed to test statistical significance, assuming two-tailed distribution and two-sample unequal variance. Values are mean±SEM and are plotted on a LOG scale. Animals (both WT and Homo) that did not seem to be conditioned after LiCl injections (meaning showing a PI for 24dMACP higher than 20% at $10^{-4}$) were excluded from our analysis (i.e. 4 WT and 2 homo).

RNA extraction and cDNA synthesis: 4•M71Cα Hemi animals were sacrificed and the olfactory epithelium tissue was dissected on a mixture of ice and dry ice. Tissue was snap frozen in liquid $N_2$ and stored at −80° C. RNA was isolated using the RNEASY® Mini columns (Qiagen, Cat #74104) with DNase digestion according the manufacturer's protocol. Tissue was homogenized with mortar and pestle in lysis buffer provided by the kit containing 10 µL ß-mercaptoethanol. The concentrations of the isolated RNA samples were measured using a NANODROP® ND-1000 Spectrophotometer. Only RNA samples with a 260/280 ratio between 1.8 and 2.1 were considered for further processing. After RNA extraction, an additional DNase digestion was performed with a TURBO DNA-FREE™ DNase Treatment and Removal (Life Technologies, cat #AM1907) kit to remove all genomic DNA (gDNA) from the sample. First-strand cDNA was synthesized using SUPERSCRIPT® III First-Strand Synthesis System for RT-PCR (Life Technologies, cat #18080-051). First-strand cDNA was diluted 1:5 to a total volume of 100 µl. Genomic contamination of the generated cDNA was checked with regular PCR using with 2 primers located in exons overspanning a small intron of the HipkII gene.:FWD 5' TGTGAGGCAATTGACATGTGG 3' (SEQ ID NO: 8) and REV 5' TACGGTGAGTCTGTGTCAC 3' (SEQ ID NO: 9).

Quantitative Real-Time PCR: qPCR was performed according to the latest Minimum Information for Publication of Quantitative Real-Time PCR Experiments (MIQE) guidelines (8) using hydrolysis probe sets. RNA was isolated form olfactory epithelial tissue from 6.5 week old littermates (4•M71Cα Hemi and WT, n=3). Amplification efficiencies of the primer/hydrolysis probe sets were calculated based upon the generation of standard curves using a 2-fold cDNA (for Gapdh, Pgk1, Tfrc, Rn18S, Omp) or plasmid DNA (for mCherry, GFP) dilution series. PCR efficiencies were calculated using the slopes of the standard curves according to the following formula: PCR $E=10^{-1/slope}-1$. The linear dynamic range was 4 dilutions and Taqman IDs, standard curve slopes, PCR efficiencies, $r^2$ values and linear dynamic range for all amplicons analyzed is summarized in Cell Reports 16, 1115-1125 (2016). The qPCR reaction mixture (10 ul) contained 5 ul TAQMAN® Gene Expression Master Mix (Applied Biosystems), 0.5 ul of the TAQMAN® probe (Applied Biosystems) and primer mix, 2.5 ul of deionized and 2 ul of cDNA. qPCR reactions were set up manually using a Matrix Electronic Multichannel Pipette with 12.5 ul Impact 384 Tips (Thermo Scientific, Hudson, NH, USA, cat #7421) and the reactions were carried out in white 384 well-plates (E&K Scientific, Inc., Santa Clara, CA, USA, cat #486384) covered with ThermaSeal optical covers (Excel Scientific, Inc., Victorville, CA, USA, cat #TSS-RTQ-100)). Reaction were run on a Roche Lightcycler 480 using the following cycling conditions: an initial denaturation step at 95° C. for 10 s, followed by a 45-cycle amplification step of 95° C. for 10 s, 60° C. for 30 s and 72° C. for 1 min and a final cooling step at 40° C. for 10 s. The Cq value for the no template controls (NTC) was >30 for all hydrolysis probe sets. qPCR levels for each hydrolysis probe set were normalized to 4 different reference genes Gapdh, Pgk1, Tfrc and Rn18S (selected based on (9)), that were stably expressed between WT and 4•M71Cα Hemi animals as shown by their coefficient of variance (CV). The CV is defined as the ratio of the standard deviation to the means and it is a useful statistic for comparing the degree of variation from one data series to another, even if the means are drastically different from each other. Reference genes with a CV lower than 25% were considered stably expressed between WT and 4•M71Cα hemi. CV's were as follows: Gapdh: 23.95%; Pgk1: 21.65%; Tfrc: 18.52% and Rn18S: 24.61%. We used the comparative Ct method or $2^{-ddCt}$ method to calculate the normalized relative quantitative (NRQ) values for each sample per gene and the fold difference in RNA expression levels.

Mitral Cell labeling: Male YFP-g mice (Strain: 014130, Jackson Laboratory) were crossed with female hemizygous 4•M71Cα (also M71G−/−) mice to generate compound mutant mice. Male offspring that were positive for both YFP and mCherry were euthanized at 8-12 weeks of age and olfactory bulb tissue was processed for histological imaging. Images were collected on a LSM510 confocal microscope (Carl Zeiss) using objectives, Fluar, 10×N.A. 0.5 and Plan-Neofluar 40×, N.A.1.3.

Immunohistochemistry: Male hemizygous 4•M71Cα (also M71G−/−), 8-12 weeks of age, were perfused transcardially with 1×PBS followed by 4% PFA. The olfactory bulbs were dissected, embedded in gelatin and postfixed overnight in 2% PFA+50% sucrose for cryoprotection. Olfactory bulbs were cryostat sectioned at 50 coronally, and processed for immunofluorescence staining. Primary antibodies: TH (1:2500, Novus), 5T4 (1:250, R&D Systems), Calretinin (1:2500, Millipore), Calbindin (1:2000, Chemicon) and CCK (1:1000, Sigma) for 2 days at 4 degrees. All sections followed by secondary antibody containing Cy5 (1:600, Jackson ImmunoResearch) incubated at room temperature for 4 hours. Images were collected on a LSM510 confocal microscope (Carl Zeiss) using objectives, Fluar, 10×N.A. 0.5 and PlanNeofluar 40×, N.A.1.3.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A vector comprising
   (a) a M71 odorant receptor (OR) transgene backbone, wherein the M71 odorant receptor (OR) transgene backbone comprises the nucleotide sequence as set forth in SEQ ID NO: 13 or 14,
   (b) at least four sequential repeats of a 21 base pair (bp) nucleotide sequence wherein each of the 21 bp sequential repeat consists of the nucleotide sequence as set forth in SEQ ID NO: 1,
   (c) a transcription start site (TSS) disposed downstream of the at least four sequential repeats, and
   (d) an odorant receptor coding sequence disposed downstream of the transcription start site.

2. The vector of claim 1, wherein the vector comprises ten or fewer sequential repeats of the 21 bp nucleotide sequence.

3. An isolated olfactory sensory neuron comprising the vector of claim 1.

4. The vector of claim 1, wherein the vector comprises at least five sequential repeats of the 21 bp nucleotide sequence.

5. The vector of claim 4, wherein the vector comprises ten or fewer sequential repeats of the 21 bp nucleotide sequence.

6. An isolated olfactory sensory neuron comprising the vector of claim 4.

\* \* \* \* \*